United States Patent
Kato et al.

(10) Patent No.: US 10,101,303 B2
(45) Date of Patent: Oct. 16, 2018

(54) CAPACITIVE MICROMACHINED ULTRASONIC TRANSDUCER AND TEST OBJECT INFORMATION ACQUIRING APPARATUS INCLUDING CAPACITIVE MICROMACHINED ULTRASONIC TRANSDUCER

(71) Applicant: CANON KABUSHIKI KAISHA, Tokyo (JP)

(72) Inventors: Ayako Kato, Machida (JP); Kazutoshi Torashima, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 72 days.

(21) Appl. No.: 14/949,482

(22) Filed: Nov. 23, 2015

(65) Prior Publication Data

US 2016/0153939 A1 Jun. 2, 2016

(30) Foreign Application Priority Data

Nov. 28, 2014 (JP) ................................. 2014-242450

(51) Int. Cl.
  *G01N 9/24* (2006.01)
  *G01N 29/24* (2006.01)
  *B06B 1/02* (2006.01)

(52) U.S. Cl.
  CPC ....... *G01N 29/2406* (2013.01); *B06B 1/0292* (2013.01)

(58) Field of Classification Search
  CPC .............. G01N 29/2406; B06B 1/0292; B81C 1/00626; H04R 1/00; H04R 2201/003; B81B 2203/04; B81B 2201/0271
  (Continued)

(56) References Cited

U.S. PATENT DOCUMENTS 6,225,651 B1 * 5/2001 Billon ............... H01L 21/76898
  257/190
8,324,006 B1 * 12/2012 Adler .................... B06B 1/0292
  257/416

(Continued)

FOREIGN PATENT DOCUMENTS

CN 101712028 A 5/2010
CN 102728533 A 10/2012
  (Continued)

OTHER PUBLICATIONS

Kwan Kyu Park, et al.; "A Comparison Between Conventional and Collapse-Mode Capacitive Micromachined Ultrasonic Transducers in 10-MHz 1-D Arrays;" IEEE Transactions on Ultrasonics, Ferroelectrics, and Frequency Control, IEEE, vol. 60, No. 6, Jun. 2013, pp. 1245-1255.

(Continued)

*Primary Examiner* — Max Noori
(74) *Attorney, Agent, or Firm* — Canon U.S.A., Inc. IP Division

(57) ABSTRACT

A capacitive micromachined ultrasonic transducer includes a first insulating film and a second insulating film disposed with a gap therebetween, a first electrode and a second electrode disposed on outer surfaces of the first and second insulating films, respectively, with the gap therebetween, at least one cell having an electrostatic capacitance between the first and second electrodes that varies with a variation of a thickness of the gap caused by displacement of the second insulating film and the second electrode, and a voltage applying unit configured to apply a voltage to between the first electrode and the second electrode. An electric field strength applied to the first insulating film is closer to an electric field strength that causes dielectric breakdown than (Continued)

an electric field strength applied to the second insulating film.

10 Claims, 10 Drawing Sheets

(58) Field of Classification Search
USPC .......................................................... 73/606
See application file for complete search history.

(56) References Cited

U.S. PATENT DOCUMENTS

| | | | | |
|---|---|---|---|---|
| 8,760,035 | B2* | 6/2014 | Tomiyoshi | B06B 1/0292 310/322 |
| 2005/0177045 | A1* | 8/2005 | Degertekin | G01N 29/2406 600/457 |
| 2005/0236937 | A1* | 10/2005 | Khuri-Yakub | B06B 1/0292 310/334 |
| 2005/0252298 | A1* | 11/2005 | Obermeier | G01L 9/0054 73/715 |
| 2006/0075818 | A1* | 4/2006 | Huang | B06B 1/0292 73/649 |
| 2007/0013269 | A1* | 1/2007 | Huang | B06B 1/0292 310/334 |
| 2007/0180916 | A1* | 8/2007 | Tian | B06B 1/0292 73/649 |
| 2007/0264732 | A1* | 11/2007 | Chen | A61B 1/041 438/22 |
| 2008/0048211 | A1* | 2/2008 | Khuri-Yakub | B06B 1/0292 257/204 |
| 2008/0194053 | A1* | 8/2008 | Huang | B06B 1/0292 438/53 |
| 2009/0018387 | A1* | 1/2009 | Veronikis | A61F 2/0045 600/37 |
| 2009/0122651 | A1* | 5/2009 | Kupnik | B06B 1/0292 367/181 |
| 2009/0142872 | A1* | 6/2009 | Park | B06B 1/0292 438/50 |
| 2010/0259127 | A1* | 10/2010 | Zaitsu | B06B 1/0292 310/300 |
| 2010/0327380 | A1* | 12/2010 | Chang | B06B 1/0292 257/419 |
| 2011/0018387 | A1* | 1/2011 | Ogawa | B06B 1/0292 310/300 |
| 2011/0073968 | A1* | 3/2011 | Ezaki | B06B 1/0292 257/416 |
| 2011/0140212 | A1* | 6/2011 | Itoh | B06B 1/0292 257/416 |
| 2011/0305822 | A1* | 12/2011 | Hasegawa | C25F 3/02 427/58 |
| 2012/0256518 | A1* | 10/2012 | Torashima | B06B 1/0292 310/300 |
| 2012/0256519 | A1 | 10/2012 | Tomiyoshi | |
| 2013/0069480 | A1* | 3/2013 | Akiyama | H02N 11/00 310/300 |
| 2013/0126993 | A1* | 5/2013 | Torashima | B06B 1/0292 257/416 |
| 2013/0135971 | A1* | 5/2013 | Nakanishi | B81C 1/00269 367/181 |
| 2014/0010388 | A1 | 1/2014 | Akiyama | |
| 2014/0313861 | A1* | 10/2014 | Torashima | B06B 1/0292 367/181 |

FOREIGN PATENT DOCUMENTS

| | | |
|---|---|---|
| CN | 103155597 A | 6/2013 |
| CN | 104113817 A | 10/2014 |
| EP | 2792423 A2 | 10/2014 |
| JP | 2008-288813 A | 11/2008 |
| WO | 2012/127737 A1 | 9/2012 |

OTHER PUBLICATIONS

B. E. Deal, et al.; "Electrical Properties of Vapor-Deposited Silicon Nitride and Silicon Oxide Films on Silicon;" J. Electrochem. Soc.: Solid State Science, Electrical Properties of Films on Si, vol. 115, No. 3, Mar. 1968, pp. 300-307.

Bads Bayram, et al.; "Capacitive Micromachined Ultrasonic Transducer Design for High Power Transmission;" IEEE Transactions on Ultrasonics, Ferroelectrics, and Frequency Control, IEEE, vol. 52, No. 2, Feb. 2005, pp. 326-339.

B. Swaroop, et al.; "Conduction in Silicon Nitride and Silicon Nitride-Oxide Films;" J. Phys. D: Appl. Phys, vol. 3, 1970, pp. 803-806.

Ayhan Bozkurt, et al.; "Theory and Analysis of Electrode Size Optimization for Capacitive Microfabricated Ultrasonic Transducers;" IEEE Transactions on Ultrasonics, Ferroelectrics, and Frequency Control, IEEE, vol. 46, No. 6, Nov. 1999, pp. 1364-1374.

* cited by examiner

CAPACITIVE MICROMACHINED ULTRASONIC TRANSDUCER AND TEST OBJECT INFORMATION ACQUIRING APPARATUS INCLUDING CAPACITIVE MICROMACHINED ULTRASONIC TRANSDUCER

BACKGROUND OF THE INVENTION

Field of the Invention

The present invention relates to a capacitive micromachined ultrasonic transducer used as, for example, an acoustic wave conversion element and a test object information acquiring apparatus including the capacitive micromachined ultrasonic transducer.

Description of the Related Art

Micro mechanical members produced using micro machining technology can perform a micrometer-scale machining operation, and a variety of micro functional elements have been developed using such micro mechanical members.

Capacitive micromachined ultrasonic transducers (CMUTs) using such technology have been researched to replace piezoelectric elements.

Capacitive micromachined ultrasonic transducers have an actuator function for transmitting an acoustic wave by vibrating a membrane (a vibrating membrane) and a sensor function for receiving the acoustic wave reflected by a test object in the form of a displacement variation of the membrane.

By using vibration of the vibrating membrane of such a capacitive micromachined ultrasonic transducer, an acoustic wave can be transmitted and received. In particular, in liquid, excellent broadband characteristics can be easily obtained. As used herein, the term "acoustic wave" refers to a sound wave, an ultrasonic wave, or a photoacoustic wave.

An acoustic wave diagnosis apparatus transmits an acoustic wave from a capacitive micromachined ultrasonic transducer to a test object and receives a reflection signal from the test object using the capacitive micromachined ultrasonic transducer. Thereafter, the acoustic wave diagnosis apparatus obtains an acoustic wave image on the basis of the received signal.

Japanese Patent Laid-Open No. 2008-288813 (hereinafter referred to as a "Patent Literature 1") describes improvement of the dielectric strength between two electrodes of a capacitive micromachined ultrasonic transducer applicable to acoustic wave diagnosis apparatuses.

The invention described in Patent Literature 1 is based on the finding that the dielectric constant of a silicon nitride film is higher than that of a silicon oxide film and the finding that a silicon nitride film easily accumulates electrical charge caused by a leakage current. More specifically, Patent Literature 1 describes a technology for increasing the dielectric strength voltage of an insulating film disposed between two electrodes that constitute a CMUT by disposing a portion of the insulating film formed from a silicon oxide film so that the portion is in contact with each of the two electrodes and disposing a portion formed from a silicon nitride film so that the portion is not in contact with the electrodes.

SUMMARY OF THE INVENTION

For example, to obtain a high transmission sound pressure level, a high voltage needs to be applied to between two electrodes that constitute a CMUT so that the displacement of the vibrating membrane is increased. However, the invention described in Patent Literature 1 aims at only increasing the dielectric strength voltage of the insulating film. That is, the invention described in Patent Literature 1 does not aim at increasing the sound pressure level and increasing the dielectric strength voltage at the same time. Thus, according to the invention described in Patent Literature 1, if the thickness of the insulating film on the vibrating membrane is increased, a capacitive micromachined ultrasonic transducer having an excellently high sound pressure level and the excellent sensitivity characteristics is not always provided.

The present invention provides a capacitive micromachined ultrasonic transducer having an excellent dielectric strength voltage in addition to an excellently high sound pressure level and the excellent sensitivity characteristics.

According to an aspect of the present invention, a capacitive micromachined ultrasonic transducer includes a first insulating film and a second insulating film disposed with a gap therebetween, a first electrode and a second electrode disposed on outer surfaces of the first and second insulating films, respectively, with the gap therebetween, at least one cell having an electrostatic capacitance between the first and second electrodes that varies with a variation of a thickness of the gap caused by displacement of the second insulating film and the second electrode, and a voltage applying unit configured to apply a voltage to between the first electrode and the second electrode. An electric field strength applied to the first insulating film is closer to an electric field strength that causes dielectric breakdown than an electric field strength applied to the second insulating film.

Further features of the present invention will become apparent from the following description of exemplary embodiments with reference to the attached drawings.

DESCRIPTION OF THE EMBODIMENTS

Figure 1:
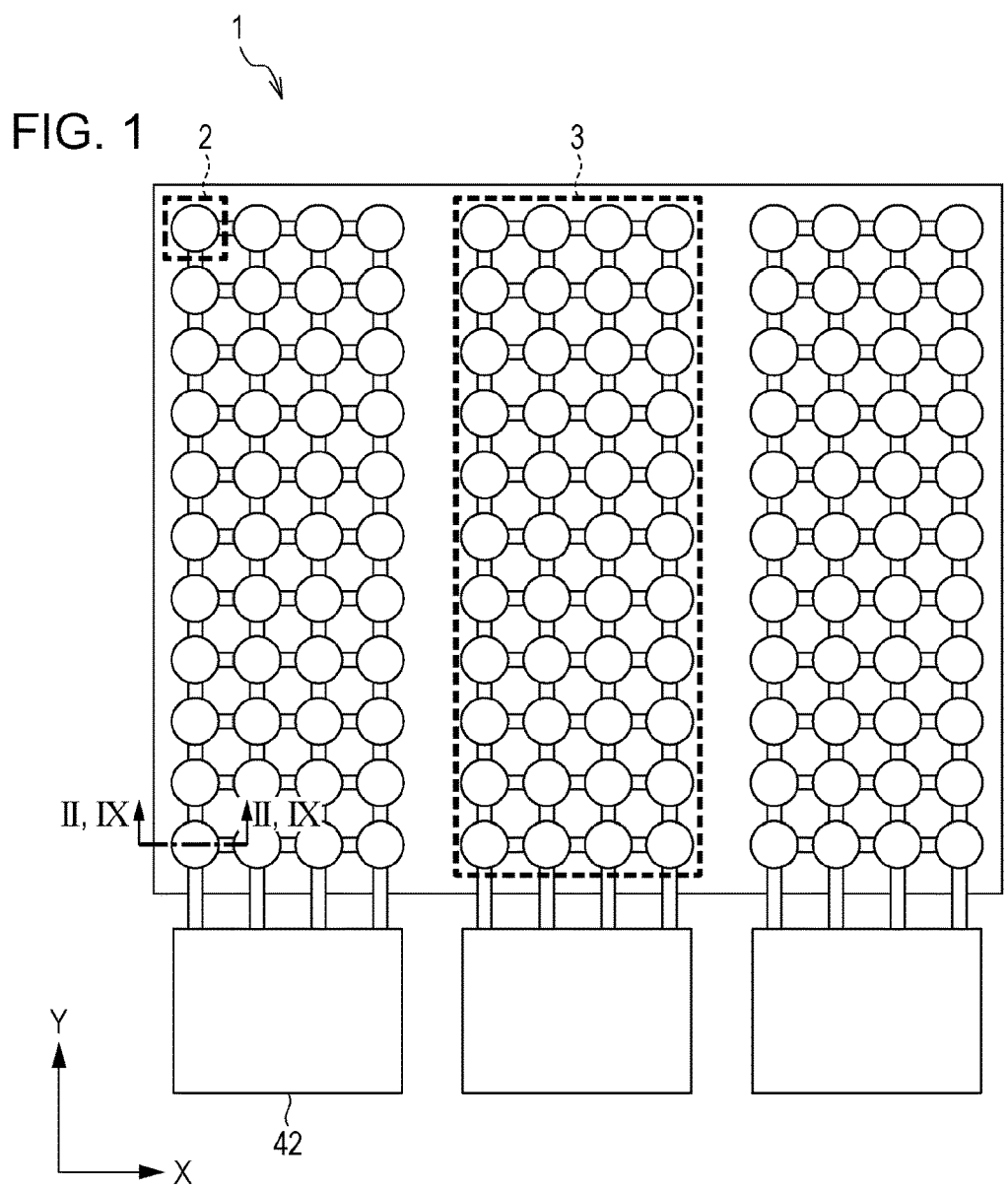
FIG. 1 is a top view of a capacitive micromachined ultrasonic transducer according to the present invention.
Figure 2:
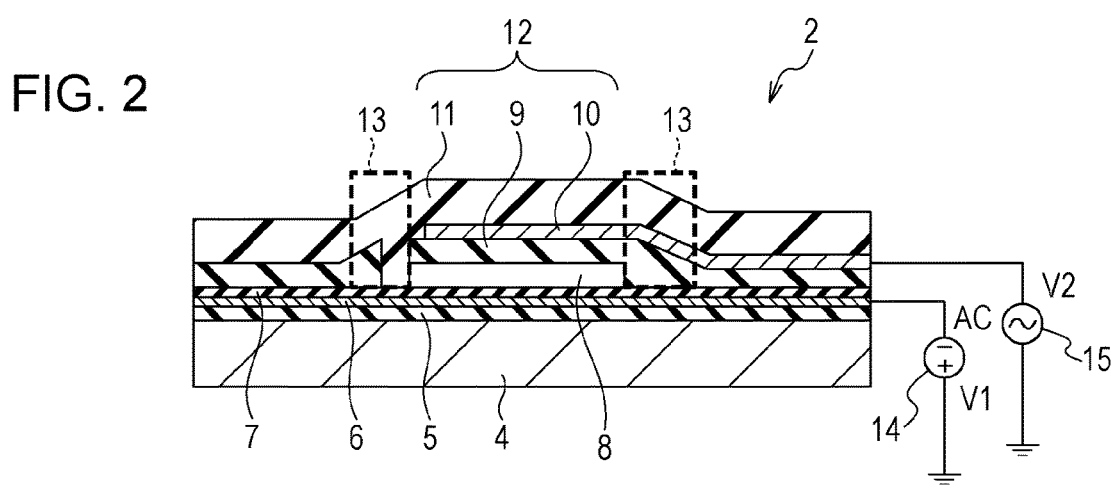
FIG. 2 is a cross-sectional view of the capacitive micromachined ultrasonic transducer taken along a line II-II of FIG. 1 according to the present invention.

A capacitive micromachined ultrasonic transducer according to the present invention is described below with reference to FIGS. 1 and 2. FIG. 1 is a schematic top view of the capacitive micromachined ultrasonic transducer according to the present invention. FIG. 2 is a cross-sectional view taken along a line II-II of FIG. 1.

In FIG. 1, a capacitive micromachined ultrasonic transducer 1, a cell 2, an element 3 formed from a plurality of the cells 2, and an electrode pad 42 for detecting an electrical current generated by the variation of the capacitance between two electrodes are illustrated.

As illustrated in FIG. 2 (a cross-sectional view of FIG. 1), the capacitive micromachined ultrasonic transducer 1 of the present invention includes a first insulating film 7 and a second insulating film 9 that are disposed with a gap (a cavity) 8 therebetween and a first electrode 6 and a second electrode 10 disposed on the outer surfaces of the first insulating film 7 and the second insulating film 9, respectively, with the gap 8 therebetween.

The capacitive micromachined ultrasonic transducer 1 further includes the cells 2 (refer to FIG. 1) and a voltage applying unit 14. In each of the cells 2, if the second insulating film 9 and the second electrode 10 are displaced, the thickness of the gap 8 varies and, thus, the capacitance between the first electrode 6 and the second electrode 10 varies. The voltage applying unit 14 applies a voltage to between the first electrode 6 and the second electrode 10. Note that FIG. 2 is a cross-sectional view of one of the cells 2 illustrated in FIG. 1.

The configuration of the present invention is characterized in that the electric field strength applied to the first insulating film 7 is closer to the electric field strength causing dielectric breakdown than the electric field strength applied to the second insulating film 9.

The capacitive micromachined ultrasonic transducer according to the present invention has a basic configuration as described above.

Before the characterized configuration is described in detail below, the members illustrated in FIG. 2 (including optional members) are described first.

As illustrated in FIG. 2, a third insulating film 5 is disposed on a substrate 4 formed of, for example, silicon. The first electrode 6 is formed on the third insulating film 5. Note that if the substrate 4 is formed from an insulating substrate, such as a glass substrate, the need for the third insulating film 5 can be eliminated.

The second electrode 10 is disposed on the second insulating film 9. A sealing film 11 is formed on the second electrode 10 as an insulating film. In this manner, a vibrating membrane 12 is formed. In this example, another insulating film is formed on the second electrode 10, and the insulating film is also displaceable.

The vibrating membrane 12 is supported by a vibration membrane support member 13. The vibration membrane support member 13 has a portion including the second electrode 10 for leading out a wire line and a portion not including the second electrode 10.

The first voltage applying unit 14 applies a voltage to between the first electrode 6 and the second electrode 10 of the cell 2. A second voltage applying unit 15 applies a transmission voltage to the second electrode 10.

The first voltage applying unit 14 can apply a bias voltage to the first electrode 6. If the bias voltage is applied to the first electrode 6, a potential difference occurs between the first electrode 6 and the second electrode 10. Due to the potential difference, the vibrating membrane 12 is displaced until the restoration force of the vibrating membrane balances the electrostatic attractive force.

At that time, if the acoustic wave reaches the vibrating membrane 12, the vibrating membrane 12 vibrates. Thus, the electrostatic capacitance between the first electrode 6 and the second electrode 10 varies, and an electrical current flows in the second electrode 10.

By retrieving the electrical current from the electrode pad 42 that is led from the second electrode 10, the acoustic wave can be detected in the form of an electrical signal.

When the bias voltage is applied to the first electrode 6 by the first voltage applying unit 14 and if a transmission voltage is applied to the second electrode 10 by the second voltage applying unit 15, an acoustic wave can be transmitted. Any transmission voltage having a waveform that allows a desired acoustic wave to be transmitted can be employed. For example, a unipolar pulse, a bipolar pulse, a burst wave, or a continuous wave can be employed.

As described above, FIG. 2 is a cross-sectional view of one of the cells 2 illustrated in FIG. 1. In FIG. 1, the top plane of the gap 8 that constitutes the cell 2 (i.e., a portion of the vibrating membrane 12 that vibrates) is circular in shape. However, the shape of the top plane of the gap 8 may be one of a variety of shapes, such as a square or a rectangle.

As illustrated in FIG. 1, three elements, for example, are formed, and each of the elements is formed by a plurality of cells 2 having a common layer that forms the first electrode 6 of each of the cells 2. That is, a plurality of cells form an element.

In FIG. 1, 44 cells 2 form each of the elements. However, the number of the cells 2 that form an element is not limited thereto. The number of the cells 2 is determined by taking into account the property of a desired ultrasonic transducer. The same applies to the number of elements.

As illustrated in FIG. 1, in addition to a grid arrangement, the arrangement of the cells 2 may be one of a plurality of arrangements, such as staggered arrangement. Furthermore, in addition to a rectangular shape illustrated in FIG. 1, the shape of a rough outline of the element 3 may be one of a plurality of shapes, such as a square or a hexagonal shape. The configuration which characterizes the present invention is described below. That is, the configuration allows the electric field strength applied to the first insulating film to be closer to the electric field strength that causes dielectric breakdown than the electric field strength applied to the second insulating film.

In FIG. 2, if the voltage applied to the first electrode 6 is increased, the electrostatic attractive force becomes higher than the restoration force of the vibrating membrane 12. Thus, the vibrating membrane 12 is brought into contact with the first insulating film 7, which is a bottom surface of the gap 8. The voltage is referred to as a "pull-in voltage". As the ratio of the bias voltage to the pull-in voltage increases, the conversion efficiency for converting the received acoustic wave to the electrical signal or converting the electrical signal to the acoustic wave increases.

If a voltage higher than or equal to the pull-in voltage is applied to between the electrodes, the vibrating membrane 12 is brought into contact with the bottom surface of the gap 8. Accordingly, the frequency characteristic of the element significantly varies and, thus, the acoustic wave receiving sensitivity that can be detected significantly varies. In addition, the strength and the frequency characteristic of the acoustic wave that can be transmitted significantly varies.

If a high voltage is applied to between the first electrode 6 and the second electrode 10 to transmit a large acoustic wave, a strong electric field is generated between the first electrode 6 and the second electrode 10.

In the element 3, the strong electric field is applied to a portion of the first insulating film 7 and a portion of the second insulating film 9 sandwiched by the first electrode 6 and the second electrode 10.

In addition, if the vibrating membrane 12 is brought into contact with the first insulating film 7 serving as the bottom surface of the gap 8, the strong electric field is also applied to the first insulating film 7 and the second insulating film 9 in the gap 8.

The dielectric strength needs to be increased to prevent dielectric breakdown of the first insulating film 7 and the second insulating film 9 when the strong electric field is applied to between the first electrode 6 and the second electrode 10.

At that time, since the second insulating film 9 forms the vibrating membrane 12 together with the second electrode 10 and the sealing film 11, the dielectric strength of the second insulating film 9 needs to be increased without changing the vibration characteristics of the vibrating membrane 12.

If the vibrating membrane 12 is configured so as to be lightweight, the characteristics (the sensitivity and the bandwidth) of the vibrating membrane 12 are increased. Accordingly, it is desirable that the second insulating film 9 that constitutes the vibrating membrane 12 be thin and lightweight.

Thus, it is desirable that the dielectric strength of the first insulating film 7 be increased instead of increasing the dielectric strength of the second insulating film.

According to the present invention, the second insulating film 9 can be configured so as to be thin and lightweight by employing the configuration in which an electric field strength that is closer to the electric field strength that causes dielectric breakdown than an electric field strength applied to the second insulating film 9 is applied to the first insulating film 7. In this manner, the vibration characteristics of the vibrating membrane 12 including the second insulating film 9 can be improved.

At that time, it is desirable that the first insulating film 7 be formed of an insulating material having a low surface roughness. This is because if the surface roughness is high, the distance between the first electrode 6 and the second electrode 10 varies from cell to cell and, thus, the vibration characteristics of the vibrating membrane varies. This variation may cause a decrease in the performance of the capacitive micromachined ultrasonic transducer 1. The surface roughness increases with increasing thickness of the insulating film. Accordingly, by setting the thickness to the smallest thickness that can retain the insulating property, degradation of the performance of the capacitive micromachined ultrasonic transducer 1 can be reduced.

It is desirable that the second insulating film 9 be formed form a film having a low tensile stress. For example, it is desirable that the film have a tensile stress of 600 MPa or lower. The stress of a silicon nitride film is controllable and, thus, the tensile stress of a silicon nitride film can be set to 600 MPa or lower.

If the second insulating film 9 has a compressive stress, sticking or buckling may occur in the vibrating membrane 12 and, thus, the vibrating membrane 12 may largely deform.

In addition, a large tensile stress causes breakdown of the vibrating membrane 12.

Accordingly, it is desirable that the vibrating membrane 12 be formed from a film of a low tensile stress. For example, it is desirable that the vibrating membrane 12 be formed from a silicon nitride film that has a controllable stress and that allows the stress to be set to a low tensile stress.

In addition, as can be understood from description of the manufacturing method of the capacitive micromachined ultrasonic transducer 1 described below (refer to FIG. 9), the second insulating film 36 is formed on a sacrifice layer 35 formed in a portion serving as the gap 8. Accordingly, it is desirable that the second insulating film 36 have a minimum thickness required for reliable coverage of the sacrifice layer 35. According to the present invention, for example, the second insulating film 36 has a minimum thickness required for the coverage, and the dielectric strength voltage is increased by the first insulating film 7.

In general, the amount of an electrical current flowing in an insulating film sandwiched by two electrodes increases with increasing electric field strength applied to the insulating film. If the electric field strength reaches a predetermined value, the insulating film is broken down.

The current-voltage characteristic of an insulating film differs depending on the type of insulating film. If electrical charge is trapped within the insulating film and moves and, in addition, the moving amount depends on the electric field strength, such a characteristic is referred to as "Poole-Frenkel conduction characteristic".

In contrast, for some insulating film, electrical charge in the insulating film does not move so much and remains at almost the same location until the electric field strength reaches a predetermined value. If the electric field strength exceeds the predetermined value, the electrical charge moves by tunneling and, thus, the amount of an electrical current rapidly increases. Such a characteristic is referred to as "Fowler-Nordheim tunneling conduction characteristic".

If each of the first insulating film 7 and the second insulating film 9 is formed from an insulating film having the Poole-Frenkel conduction characteristic, the electrical charge moves in accordance with the electric field strength applied to between the first electrode 6 and the second electrode 10. Thus, the electrical charge is accumulated in the insulating film. If the electrical charge is accumulated in the insulating film and, thus, the insulating film is charged, the drive voltage varies. In addition, the vibration characteristic of the vibrating membrane varies. Consequently, the performance of the capacitive micromachined ultrasonic transducer 1 decreases.

Thus, according to the present invention, it is desirable that the first insulating film 7 be formed from an insulating film having Fowler-Nordheim tunneling conduction characteristic. In this manner, electrical charge does not move so much and is not accumulated in the insulating film until the electric field strength reaches the value at which tunneling occurs. Thus, a decrease in the performance of the capacitive micromachined ultrasonic transducer 1 can be prevented.

In addition, at that time, by setting the electrical potential of the first electrode 6 with which the first insulating film 7 is brought into contact to a value lower than the electrical potential of the second electrode 10, the second insulating film 9 can be made to be an insulating film having Pool-Frenkel conduction characteristic.

Figure 3:
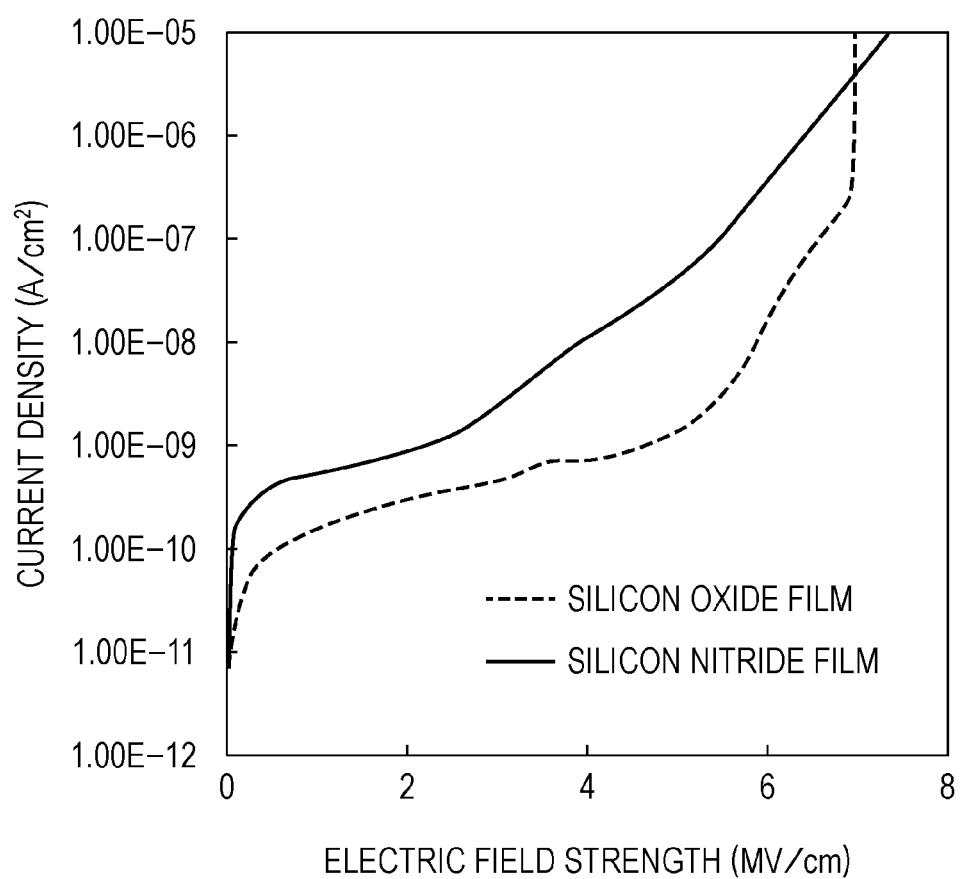
FIG. 3 illustrates an example of the current-voltage characteristics of insulating films of the capacitive micromachined ultrasonic transducer according to the present invention.

FIG. 3 illustrates an example of the current-voltage characteristics of the insulating films. An example of the current-voltage characteristic of a silicon nitride film is shown as a solid line, and an example of the current-voltage characteristic of a silicon oxide film is shown as a dotted line.

According to the present invention, it is desirable that a silicon oxide film be employed as the insulating film having the Fowler-Nordheim tunneling conduction characteristic and the silicon nitride film be employed as the insulating film having the Poole-Frenkel conduction characteristic. In general, the dielectric breakdown occurs if the current density exceeds $1.0 \times 10^{-8}$ (A/cm$^2$).

In addition, if an electric field strength that is higher than a predetermined value is applied to an insulating film having the Fowler-Nordheim tunneling conduction characteristic, electrical charge moves in the insulating film by tunneling and, thus, the amount of an electrical current abruptly increases. Accordingly, it is desirable that the electric field strength at which the current density abruptly changes be the same as the electric field strength at which the dielectric breakdown occurs.

For example, in the case of the silicon oxide film illustrated in FIG. 3, the electric field strength at which the current density abruptly changes is 5.12 (MV/cm).

In addition, the electric field strength at which the dielectric breakdown of the silicon nitride film occurs is 4 (MV/cm).

When two types of insulating film are disposed between the first electrode 6 and the second electrode 10 and if a voltage V is applied to between the first electrode 6 and the second electrode 10, a relationship between a voltage V1 applied to the first insulating film 7 and a voltage V2 applied to the second insulating film 9 is given as follows:

$$V = V1 + V2 \quad (1).$$

Let t1 be the thickness of the first insulating film, and let E1 be the electric field strength. Then, the voltage V1 applied to the first insulating film 7 is expressed as follows:

$$V1 = t1 \times E1 \quad (2).$$

Let t2 be the thickness of the second insulating film, and let E2 be the electric field strength. Then, the voltage V2 applied to the second insulating film 9 is expressed as follows:

$$V2 = t2 \times E2 \quad (3).$$

Let $\in 1$ be the relative permittivity of the first insulating film, and let $\in 2$ be the relative permittivity of the second insulating film. Then, since the product of the relative permittivity and the electric field strength is conserved, the following equation is obtained:

$$\in 1 \times E1 = \in 2 \times E2 \quad (4).$$

From Equations (1), (2), and (3), the following equation is obtained:

$$V = t1 \times E1 + t2 \times E2 \quad (5).$$

From Equation (4), the following equation is obtained:

$$E2 = \in 1 \times E1 / \in 2, \text{ and}$$

$$E1 = \in 2 \times E2 / \in 1 \quad (6).$$

From Equations (5) and (6), the following equation is obtained:

$$t1 = ((\in 1 \times V/E2) - (t2 \times \in 1))/\in 2 \quad (7).$$

In addition, when the voltage V is applied to between the first electrode 6 and the second electrode 10, the ratio of the voltage V1 applied to the first insulating film 7 to the voltage V and the ratio of the voltage V2 applied to the second insulating film to the voltage V are given as follows.

That is, from Equations (5) and (6), the following equations can be obtained:

$$V = E1 \times (t1 + t2 \times \in 1/\in 2) \quad (6\text{-}2), \text{ and}$$

$$V = E2 \times (t2 + t1 \times \in 2/\in 1) \quad (6\text{-}3).$$

From Equations (2) and (6-2), the following equation is obtained:

$$V1/V = t1 \times \in 2/(\in 2 \times t1 + t2 \times \in 1) \quad (8).$$

From Equations (2) and (6-3), the following equation is obtained:

$$V2/V = t2 \times \in 1/(\in 2 \times t1 + t2 \times \in 1) \quad (9).$$

A voltage VV1 at which dielectric breakdown of the first insulating film occurs is given as follows:

$$VV1 = t1 \times E1/(V1/V) \quad (10).$$

In addition, a voltage VV2 at which dielectric breakdown of the second insulating film occurs is given as follows:

$$VV2 = t2 \times E2/(V2/V) \quad (11).$$

For example, to determine the vibration characteristic of the vibrating membrane 12, the thickness t2 of the second insulating film is set to 0.3 μm, and the voltage V applied to between the first electrode 6 and the second electrode 10 is set to 250 V.

If the second insulating film 9 is formed from a silicon nitride film, the electric field strength at which the dielectric breakdown of the second insulating film 9 occurs is 4 (MV/cm). The electric field strength at which dielectric breakdown of the first insulating film 7 occurs is 5.12 (MV/cm) in the case of a silicon oxide film. In addition, the relative permittivity of the first insulating film is 4.4, and the relative permittivity of the second insulating film is 6.8.

From Equation (7), the thickness t1 of the first insulating film 7 is 0.2942 μm. By setting the thickness to a value greater than or equal to this value, the dielectric breakdown of the first insulating film does not occur.

Since in terms of the surface roughness, it is desirable that the thickness of the first insulating film 7 be small, the thickness of the first insulating film 7 is set to 0.3 μm.

At that time, from Equation (8), the ratio of the voltage V1 applied to the first insulating film to the voltage V is 0.607. From Equation (9), the ratio of the voltage V2 applied to the second insulating film to the voltage V is 0.393.

From Equation (10), the voltage VV1 at which the dielectric breakdown of the first insulating film occurs is given as follows:

$$VV1 = 0.3 \text{ μm} \times 5.12 \text{ (MV/cm)}/0.607 = 253.05 \text{ V}.$$

In addition, from Equation (11), the voltage VV2 at which the dielectric breakdown of the second insulating film occurs is given as follows:

$$VV2 = 0.3 \text{ μm} \times 4 \text{ (MV/cm)}/0.393 = 305.34 \text{ V}.$$

As can be seen from the above description, since the applied voltage V is lower than each of the voltages V1 and V2 that cause the dielectric breakdown of the first insulating film 7 and the second insulating film 9, respectively, the dielectric breakdown can be prevented.

In addition, the electric field strength applied to the first insulating film 7 is calculated as follows:

voltage V1 applied to the first insulating film/thickness of the first insulating film=5.06 (MV/cm).

In addition, the electric field strength applied to the second insulating film 9 is calculated as follows:

voltage V2 applied to the second insulating film/thickness of the second insulating film=3.26 (MV/cm).

That is, the electric field strength applied to the first insulating film 7 is closer to the electric field strength at which the dielectric breakdown occurs than the electric field strength applied to the second insulating film 9.

At that time, the value obtained by dividing the electric field strength at which the dielectric breakdown of the first insulating film 7 occurs by the electric field strength at which the dielectric breakdown of the second insulating film 9 occurs is 1.28.

In addition, the value obtained by dividing the relative permittivity of the second insulating film 9 by the relative permittivity of the first insulating film 7 is 1.55.

By setting the configurations of the first insulating film 7 and the second insulating film 9 to the above-described configurations, the dielectric strength voltage can be increased without changing the vibration characteristic of the vibrating membrane.

The effect of the electric field strength that is close to the electric field strength at which the dielectric breakdown occurs according to the present invention is described below.

From Equations (6-2) and (6-3), the following equations are obtained for the electric field strengths E1 and E2:

$$E1 = V/(t1 + t2 \times \in 1/\in 2) \quad (12), \text{ and}$$

$$E2 = V/(t2 + t1 \times \in 2/\in 1) \quad (13).$$

Let EX1 be the electric field strength that causes dielectric breakdown of the first insulating film, and let EX2 be the electric field strength that causes dielectric breakdown of the second insulating film. Then, according to the present invention, it is desirable that the configuration satisfy the following expression:

$$E1/EX1 > E2/EX2 \quad (14).$$

The current-voltage characteristic of the insulating film illustrated in FIG. 3 as an example may vary depending on the film forming conditions and the type of material for forming a film.

Figure 4:
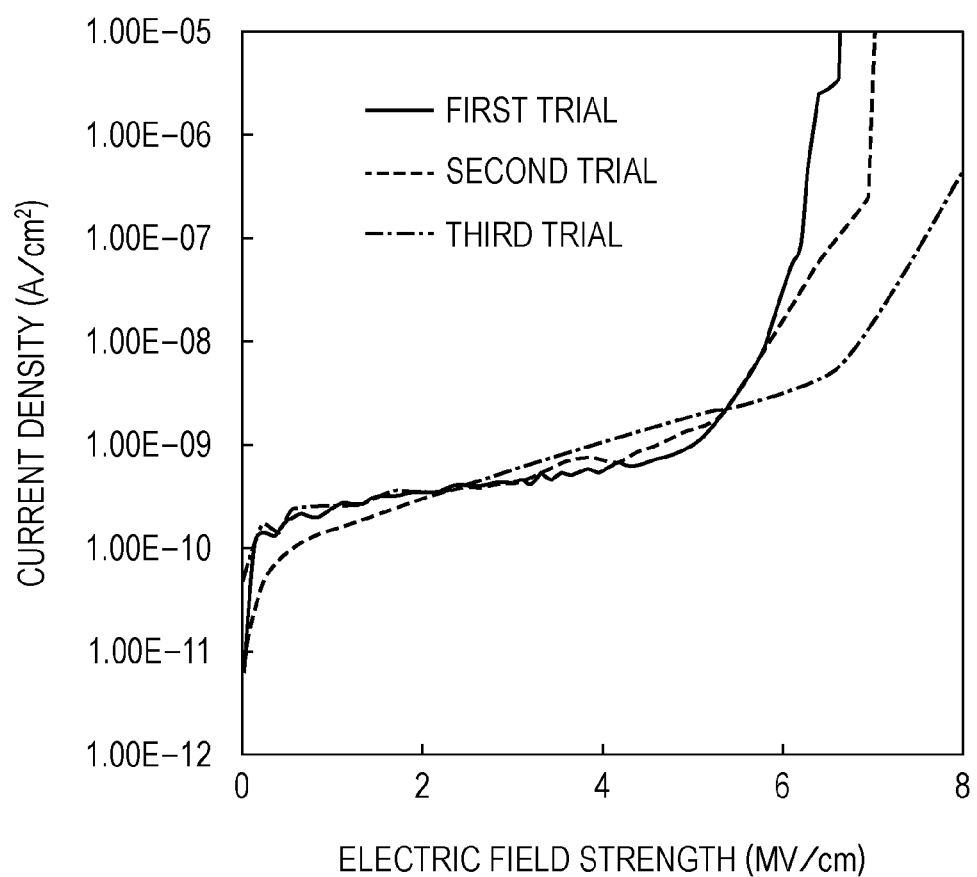
FIG. 4 is a graph illustrating an example of the current-voltage characteristic of a first insulating film of the capacitive micromachined ultrasonic transducer according to the present invention.
Figure 5:
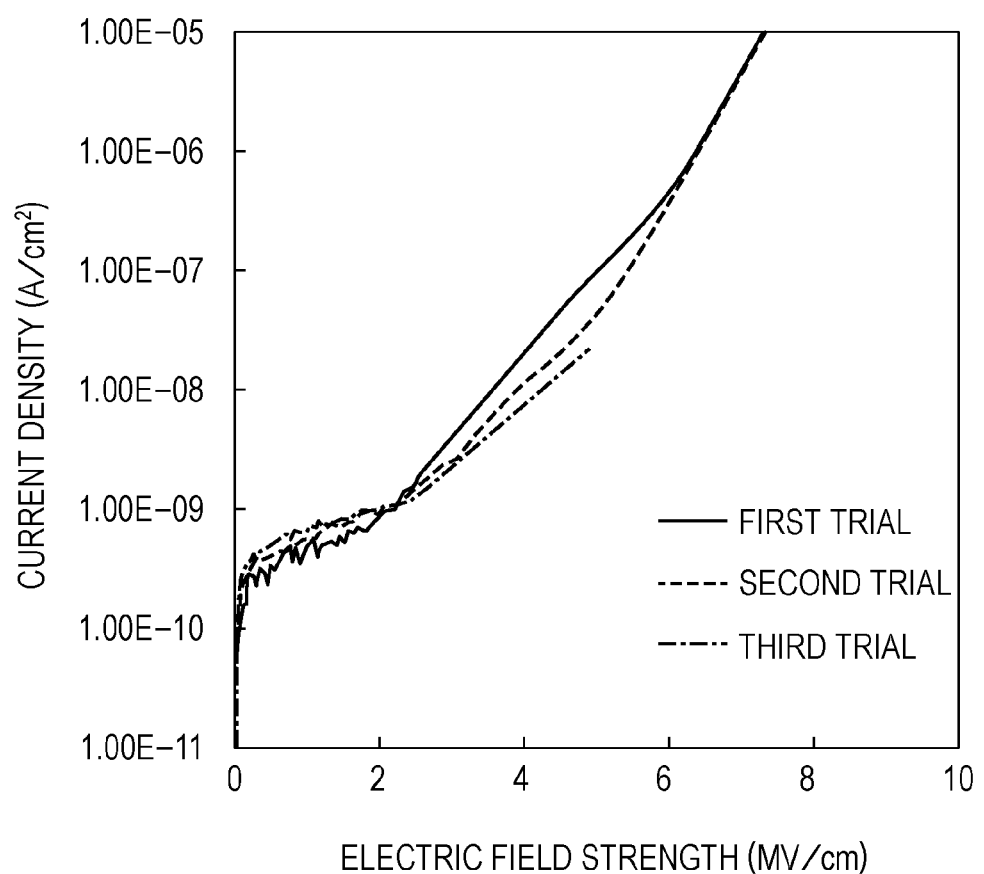
FIG. 5 is a graph illustrating an example of the current-voltage characteristic of a second insulating film of the capacitive micromachined ultrasonic transducer according to the present invention.

The current-voltage characteristics of the insulating films that are formed at different time points are illustrated in FIGS. 4 and 5.

FIG. 4 illustrates the current-voltage characteristic of a silicon oxide film, and FIG. 5 illustrates the current-voltage characteristic of a silicon nitride film.

More specifically, FIG. 4 illustrates the result of measurement of the current-voltage characteristic after forming a silicon oxide film through three trials at different time points. In the first trial, the electric field strength at which the current density abruptly changes is 4.8 (MV/cm). In the second trial, the electric field strength at which the current density abruptly changes is 5.12 (MV/cm). In the third trial, the electric field strength at which the current density abruptly changes is 6.0 (MV/cm).

FIG. 5 illustrates the result of measurement of the current-voltage characteristic after forming a silicon nitride film through three trials at different time points. In the first trial, the electric field strength at which the current density exceeds $1.0 \times 10^{-8}$ (A/cm$^2$) is 3.0 (MV/cm). In the second trial, the electric field strength at which the current density exceeds $1.0 \times 10^{-8}$ (A/cm$^2$) is 4.0 (MV/cm). In the third trial, the electric field strength at which the current density exceeds $1.0 \times 10^{-8}$ (A/cm$^2$) is 4.2 (MV/cm).

It is desirable that the value of the electric field strength at which the dielectric breakdown occurs be determined by forming an insulating film in advance under the conditions under which the insulating layer is to be formed when the capacitive micromachined ultrasonic transducer is fabricated and measuring the current-voltage characteristic of the formed insulating film.

If the variation per film forming is taken into account, the smallest value obtained by dividing the electric field strength at which the dielectric breakdown of the first insulating film 7 by the electric field strength at which the dielectric breakdown of the second insulating film 9 is 1.14.

Since the relationship between the relative permittivity of the insulating film and the electric field strength is expressed as $\in 2/\in 1 = E1/E2$, it is desirable to employ an insulating film having a value obtained by dividing the relative permittivity of the second insulating film 9 by the relative permittivity of the first insulating film 7 being greater than 1.14.

If such an insulating film is employed, the electric field strength applied to the first insulating film 7 is closer to the electric field strength that causes the dielectric breakdown than the electric field strength applied to the second insulating film 9.

In addition, the value of the electric field strength that causes the dielectric breakdown includes a measurement variation of a measurement apparatus that is used to measure the current and the voltage of the insulating film. Furthermore, the value of the dielectric constant includes a measurement variation. Still furthermore, the value of the voltage applied to between the first electrode 6 and the second electrode 10 includes a voltage variation of the power supply.

Accordingly, it is desirable that the thickness of the insulating film be determined so that the electric field strength applied to the first insulating film 7 and the electric field strength applied to the second insulating film 9 do not reach the electric field strength that causes the dielectric breakdown by taking into account such variations and the variation of the voltage. For example, a total of the variations may be estimated as 5%, and the electric field strength applied to the first insulating film 7 and the electric field strength applied to the second insulating film 9 may be set to a value less than or equal to 95% of the electric field strength that causes the dielectric breakdown.

As described above, to determine the vibration characteristic of the vibrating membrane 12, the thickness t2 of the second insulating film 9 is determined. In addition, the highest voltage V applied to between the first electrode 6 and the second electrode 10 is determined, and the thickness t1 of the first insulating film 7 is determined. In this manner, the dielectric strength voltage can be increased without changing the vibration characteristic of the vibrating membrane.

Figure 6:
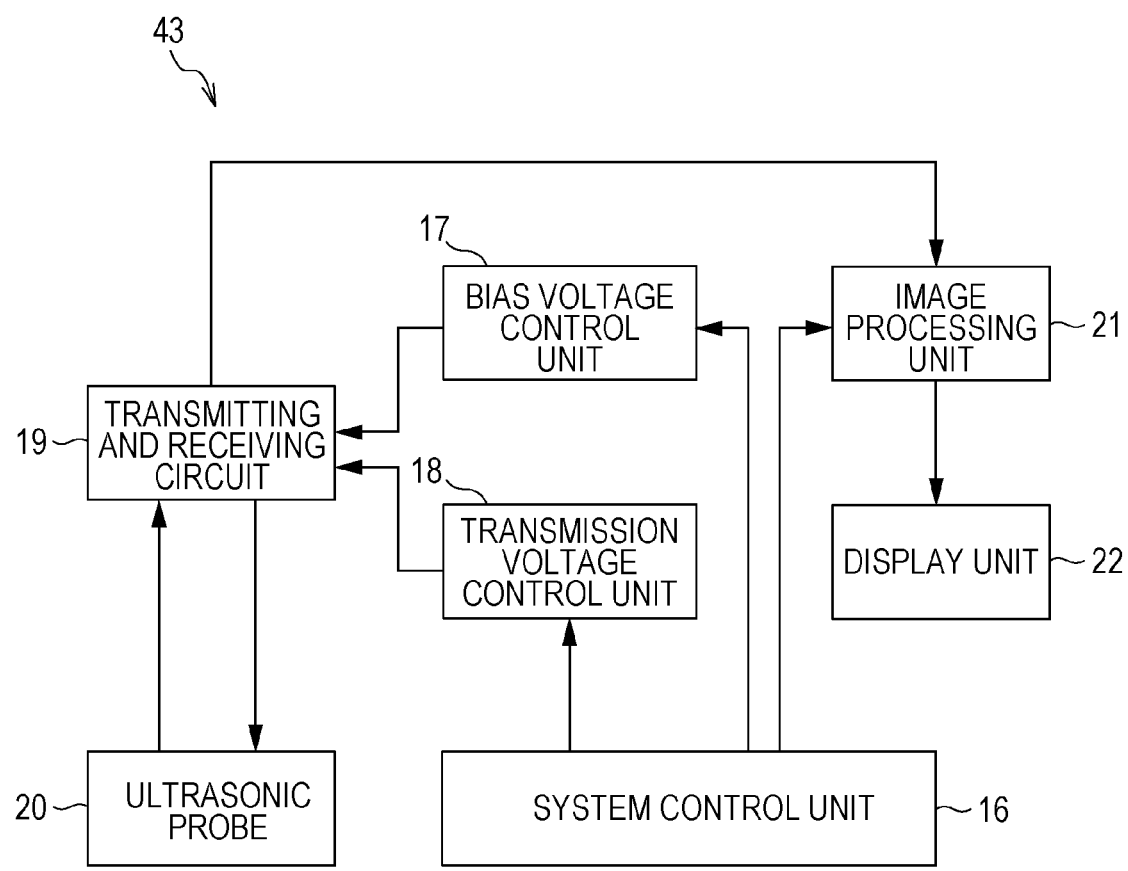
FIG. 6 illustrates a test object information acquiring apparatus having the capacitive micromachined ultrasonic transducer applied thereto according to the present invention.

FIG. 6 illustrates an example of a test object information acquiring apparatus having the capacitive micromachined ultrasonic transducer applied thereto according to the present invention.

The test object information acquiring apparatus 43 includes a system control unit 16, a bias voltage control unit 17, a transmission voltage control unit 18, a transmitting and receiving circuit (circuit unit) 19, an ultrasonic probe 20, an image processing unit 21, and a display unit 22.

The ultrasonic probe 20 is a transmission and reception probe formed from the capacitive micromachined ultrasonic transducer 1 of the present invention. The ultrasonic probe 20 transmits an acoustic wave to a test object and receives the acoustic wave reflected by the test object.

The transmitting and receiving circuit (circuit unit) 19 supplies, to the ultrasonic probe 20, a bias voltage externally supplied and the drive voltage. In addition, the transmitting and receiving circuit 19 processes the acoustic wave received by the ultrasonic probe 20 and outputs the result of processing to the image processing unit 21.

The bias voltage control unit 17 supplies the bias voltage to the transmitting and receiving circuit 19 to supply the bias voltage to the ultrasonic probe 20. The bias voltage control unit 17 includes a power supply (not illustrated) and a switch. The bias voltage control unit 17 supplies the bias voltage to the transmitting and receiving circuit 19 at a time point indicated by the system control unit 16.

The transmission voltage control unit 18 supplies a transmission voltage to the transmitting and receiving circuit (circuit unit) 19 to supply the transmission voltage to the ultrasonic probe 20. The transmission voltage control unit 18 supplies a waveform that provides desired frequency characteristic and transmission sound pressure to the transmitting and receiving circuit (circuit unit) 19 at a time point indicated by the system control unit 16.

The image processing unit 21 performs image conversion (e.g., a B mode image or an M mode image) using the signal output from the transmitting and receiving circuit 19 and outputs the converted image to the display unit 22.

The display unit 22 is formed from a display apparatus that displays the image signal output from the image processing unit 21. The display unit 22 can be separated from the body of the test object information acquiring apparatus 43.

The system control unit 16 is a circuit that controls the bias voltage control unit 17, the transmission voltage control unit 18, and the image processing unit 21.

Figure 7:
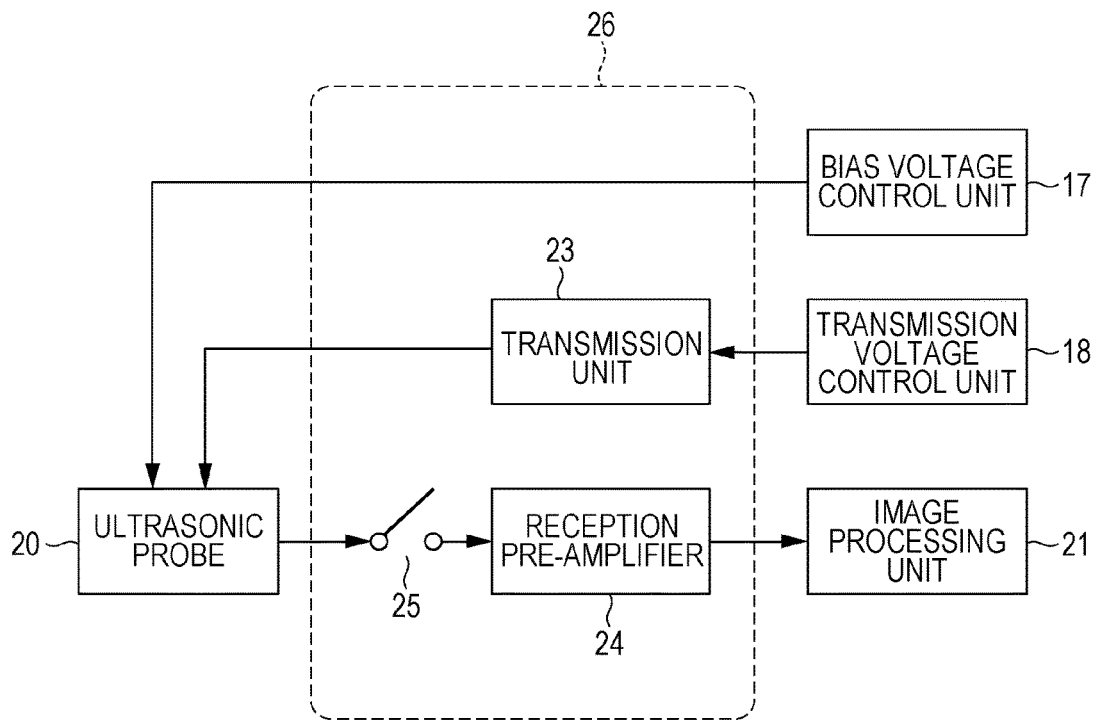
FIG. 7 illustrates an example of the transmitting and receiving circuit that drives the capacitive micromachined ultrasonic transducer according to the present invention.

FIG. 7 illustrates an example of the transmitting and receiving circuit. A transmitting and receiving circuit 26 includes a transmission unit 23, a reception pre-amplifier 24, and a switch 25.

When controlling a transmission operation, the transmitting and receiving circuit 26 applies, to the ultrasonic probe 20, the bias voltage applied by the bias voltage control unit 17 in accordance with a transmission bias voltage indicated by the system control unit 16 illustrated in FIG. 6.

Similarly, the transmitting and receiving circuit 26 applies, to the ultrasonic probe 20, the voltage applied by the transmission voltage control unit 18 via the transmission unit 23 in accordance with the transmission voltage indicated by the system control unit 16.

If the transmission voltage is applied, the switch 25 is open and, thus, a signal sent to the reception pre-amplifier 24 is blocked. However, if the transmission voltage is not applied, the switch 25 is closed and, thus, the transmitting and receiving circuit 26 enters a reception mode.

The switch 25 is formed from, for example, diodes (not illustrated). The switch 25 functions as a protection circuit that protects the reception pre-amplifier 24 from being broken down.

When an acoustic wave is transmitted from the ultrasonic probe 20 and if the acoustic wave is reflected back from the test object to the ultrasonic probe 20, the ultrasonic probe 20 receives the acoustic wave.

In reception, the transmitting and receiving circuit 26 applies, to the ultrasonic probe 20, the bias voltage applied by the bias voltage control unit 17 in accordance with a reception bias voltage indicated by the system control unit 16 illustrated in FIG. 6. Since the switch 25 is closed, the received signal is amplified by the reception pre-amplifier 24 and is sent to the image processing unit 21.

Figure 8:
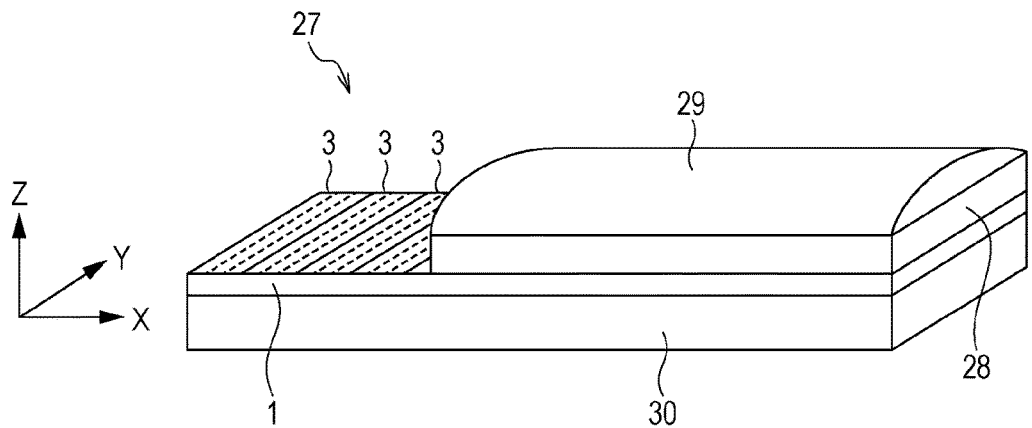
FIG. 8 is a perspective view of an ultrasonic probe including the capacitive micromachined ultrasonic transducer according to the present invention.

An example of the ultrasonic probe is illustrated in FIG. 8.

FIG. 8 is a perspective view of the ultrasonic probe. An ultrasonic probe 27 includes the capacitive micromachined ultrasonic transducer 1, an acoustic matching layer 28, an acoustic lens 29, and a circuit substrate 30.

The capacitive micromachined ultrasonic transducer 1 illustrated in FIG. 8 has a configuration similar to that of the capacitive micromachined ultrasonic transducer 1 illustrated in FIG. 1. As illustrated in FIG. 8, a plurality of elements 3 are arranged in the X-direction in a one-dimensional array.

Although the elements 3 are arranged in a one-dimensional array in FIG. 8, the elements 3 may be arranged in a two-dimensional array. Alternatively, the elements 3 may be arranged in another shape, such as a convex array shape.

The capacitive micromachined ultrasonic transducer 1 is mounted on the circuit substrate 30 and is electrically connected to the circuit substrate 30. The circuit substrate 30 may be a substrate integrated with the transmitting and receiving circuit 19 illustrated in FIG. 6. Alternatively, the capacitive micromachined ultrasonic transducer 1 may be electrically connected to the transmitting and receiving circuit 19 illustrated in FIG. 6 via the circuit substrate 30.

To provide acoustic impedance matching with the test object, an acoustic matching layer 28 is formed on the front surface of the circuit substrate 30 from which the capacitive micromachined ultrasonic transducer 1 transmits the acoustic wave.

The acoustic matching layer 28 may be formed as a protective film that prevents a leakage current from flowing to the test object.

The acoustic lens 29 is disposed on the acoustic matching layer 28. It is desirable that the acoustic lens 29 that can provide impedance matching between the test object and the acoustic matching layer 28 be employed.

By providing the acoustic lens 29 having a curvature in the Y-direction as illustrated in FIG. 8, the acoustic wave that expands in the Y-direction can be focused at the focal position of the acoustic lens. In contrast, the acoustic wave that expands in the X-direction cannot be focused without using an appropriate technique. Accordingly, by controlling a transmission operation so that the acoustic wave is sequentially transmitted to each of the elements 3 by beamforming, the acoustic wave can be focused at the focal position of the acoustic lens.

It is desirable that the shape of the acoustic lens 29 be a shape having a desired acoustic wave distribution characteristic. In addition, one of a variety of types and shapes of the acoustic matching layer 28 and the acoustic lens 29 can be selected in accordance with the type of test object to be measured. Alternatively, the need for the acoustic matching layer 28 or the acoustic lens 29 may be eliminated in accordance the type of test object to be measured. The bias voltage and the transmission voltage are supplied to the ultrasonic probe 27 via a cable (not illustrated). In addition, the received signal in the acoustic wave reflected from a test object is transmitted to the transmission voltage control unit 18 or the image processing unit 21 via a cable (not illustrated). An example of a method for manufacturing the capacitive micromachined ultrasonic transducer of the present invention is described below with reference to FIGS. 9A to 9E and FIGS. 10A and 10B.

FIGS. 9A to 9E are cross-sectional views taken along a line IX-IX of FIG. 1.

Figure 9A:
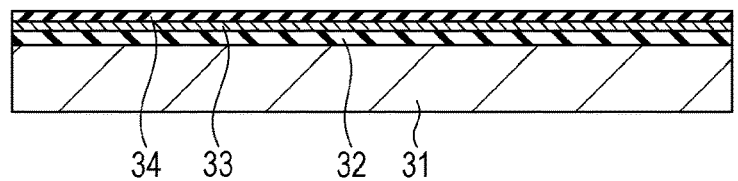
FIGS. 9A to 9E illustrate a method for manufacturing the capacitive micromachined ultrasonic transducer according to the present invention.

As illustrated in FIG. 9A, a third insulating film 32 is formed on a substrate 31. The substrate 31 is formed from a silicon substrate. The third insulating film 32 electrically insulate the silicon substrate 31 from a first electrode. If the substrate 31 is an insulating substrate, such as a glass substrate, the need for forming the third insulating film 32 can be eliminated. In addition, it is desirable that the substrate 31 have a low surface roughness. If the substrate 31 have a high surface roughness, the surface roughness is transferred in a film forming step subsequent to this step and, in addition, the distance between the first electrode and a second electrode varies from cell to cell due to the surface roughness. This variation causes a variation of the conversion efficiency. Thus, the sensitivity and the frequency vary. Accordingly, it is desirable that the substrate 31 have a low surface roughness.

Subsequently, a first electrode 33 is formed. It is desirable that the first electrode 33 be formed of a conductive material having a low surface roughness. For example, titanium, tungsten, or aluminum can be employed. Like the substrate, if the surface roughness of the first electrode 33 is high, the distance between the first electrode and the second electrode varies from cell to cell due to the surface roughness. Accordingly, it is desirable that a conductive material having a low surface roughness be employed.

Subsequently, a first insulating film 34 is formed. It is desirable that the first insulating film 34 be formed of an insulating material having a low surface roughness. The first insulating film 34 is formed to prevent short circuit between the first electrode and the second electrode and dielectric breakdown when a voltage is applied to between the first electrode and the second electrode. In addition, the first insulating film 34 is formed to prevent the first electrode from being etched when a sacrifice layer is removed in a step subsequent to this step. Like the substrate, if the surface roughness of the first insulating film 34 is high, the distance between the first electrode and the second electrode varies from cell to cell due to the surface roughness. Accordingly, it is desirable that an insulating film having a low surface roughness be employed. For example, a silicon nitride film or a silicon oxide film is desirable. In particular, as described above, according to the present invention, a silicon oxide film is desirable. Note that since the surface roughness of the insulating film increases with increasing thickness thereof, the thickness is set to a minimum value required for retaining electrical insulation.

If a silicon oxide film is employed as the first insulating film, a thickness in the range from 10 nm to 1000 nm is desirable, and a thickness in the range from 50 nm to 500 nm is more desirable.

Figure 9B:
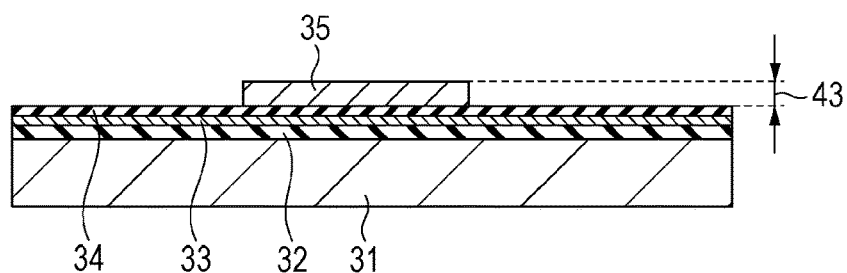

Subsequently, as illustrated in FIG. 9B, a sacrifice layer 35 is formed. The thickness of the sacrifice layer 35 is represented as a gap G 43. The sacrifice layer 35 is made into the gap G (a cavity) 43 later. It is desirable that the sacrifice layer 35 be formed of a material having a low surface roughness. Like the substrate, if the surface roughness of the sacrifice layer 35 is high, the distance between the first electrode and the second electrode varies from cell to cell due to the surface roughness. Accordingly, it is desirable that the sacrifice layer 35 having a low surface roughness be employed.

In addition, to reduce the time period required for etching for removing the sacrifice layer, it is desirable that the sacrifice layer be formed of a material having a high etching rate. In addition, it is required that the sacrifice layer be formed of a material that prevents the insulating film and the vibrating membrane from being etched by an etching solution or etching gas used to remove the sacrifice layer.

If the insulating film or the vibrating membrane is etched by an etching solution or etching gas used to remove the sacrifice layer, a variation of the thickness of the vibrating membrane and a variation of the distance between the first electrode and the second electrode occur. The variation of the thickness of the vibrating membrane and the variation of the distance between the first electrode and the second electrode cause a variation of the sensitivity and a variation of the frequency from cell to cell.

If the insulating film and the vibrating membrane are formed from a silicon nitride film or a silicon oxide film, it is desirable that the sacrifice layer be formed of a material that has a low surface roughness and that allows an etching solution or etching gas which negligibly etches the insulating film and the vibrating membrane to be used.

Examples of the material include amorphous silicon, polyimide, and chrome. In particular, since an etching solution for the chrome negligibly etches the silicon nitride film and the silicon oxide film, it is desirable that chrome be employed when the insulating film and the vibrating membrane are formed from a silicon nitride film or a silicon oxide film.

Figure 9C:
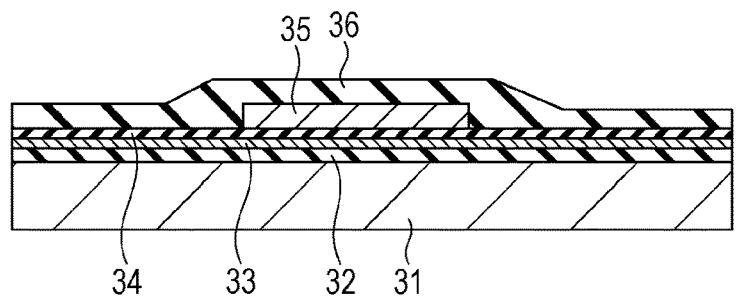

Subsequently, as illustrated in FIG. 9C, a second insulating film 36 is formed. It is desirable that the second insulating film 36 be formed from a film having a low tensile stress. For example, it is desirable that the second insulating film 36 be formed from a film having a tensile stress of 500 MPa or lower. The stress of a silicon nitride film is controllable and, thus, the stress of a silicon nitride film can be adjusted to a low value lower than or equal to 500 MPa.

If the vibrating membrane has a compressive stress, sticking or buckling may occur in the vibrating membrane and, thus, the vibrating membrane may largely deform. In addition, in the case of a large tensile stress, the second insulating film 36 may be broken down.

Accordingly, it is desirable that the second insulating film 36 have a low tensile stress. For example, the second insulating film 36 is formed from the silicon nitride film having a stress that is controllable so as to have a low tensile stress. In addition, to form a layer on the sacrifice layer 35, it is desirable that the thickness of the second insulating film 36 have a thickness that can reliably provide coverage of the sacrifice layer 35.

If a silicon nitride film is employed as the second insulating film, it is desirable that the thickness of the silicon nitride film be in the range from 10 nm to 1000 nm and more preferably in the range from 50 nm to 900 nm.

Figure 11:
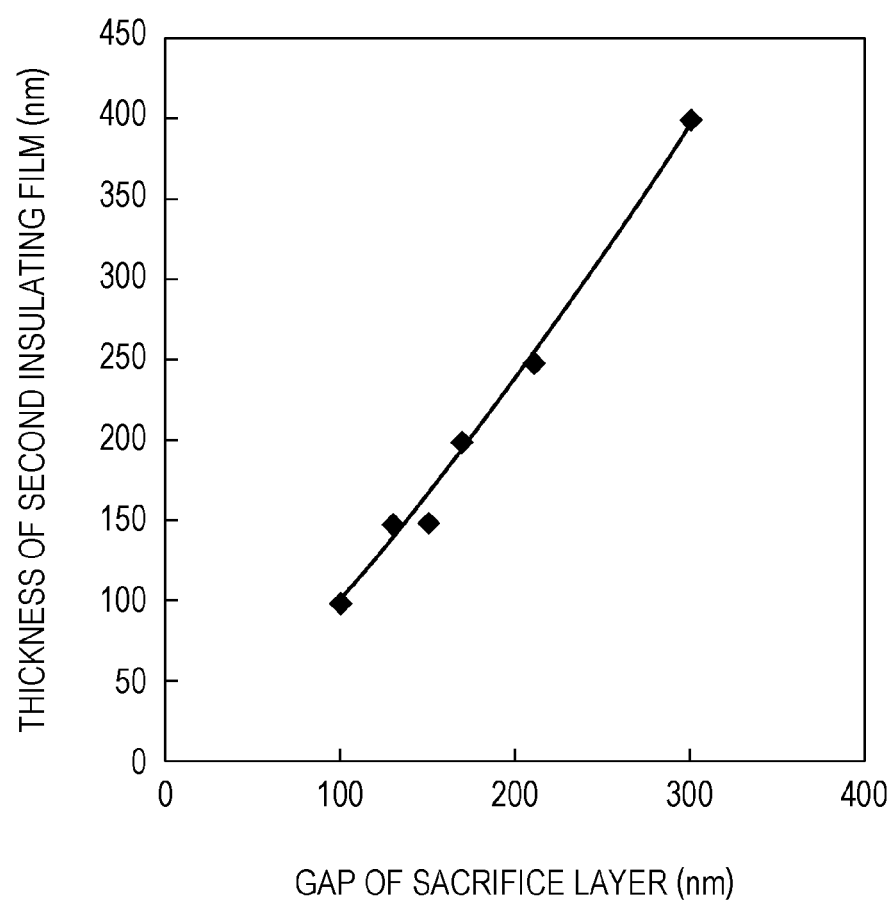
FIG. 11 illustrates an example of a relationship between a gap G and the thickness of the second insulating film of the capacitive micromachined ultrasonic transducer according to the present invention.

FIG. 11 illustrates an example of a relationship between the gap G 43 illustrated in FIG. 9B and the thickness of the second insulating film 36 that is required for reliably providing the coverage of the gap G 43. In FIG. 11, the abscissa represents the gap G, and the ordinate represents the thickness of the second insulating film 36.

A film was formed by changing the thickness of the second insulating film 36 with respect to the thickness of the sacrifice layer 35 that was made into the gap G 43. A sample of the formed film was immersed in the etching solution used for the sacrifice layer 35, and damage of the second insulating film 36 was observed by a microscope. In this manner, the thickness of the second insulating film 36 that was required for reliably providing the coverage of the gap G 43 was obtained.

The thickness of the second insulating film required for reliably providing the coverage of the gap G is a thickness greater than or equal to $0.32 \times G^{1.24}$, where G represents the thickness of the gap.

By setting the thickness of the second insulating film 36 to a value greater than or equal to $0.32 \times G^{1.24}$ with respect to the gap G, a reliable capacitive micromachined ultrasonic transducer can be produced.

Figure 9D:
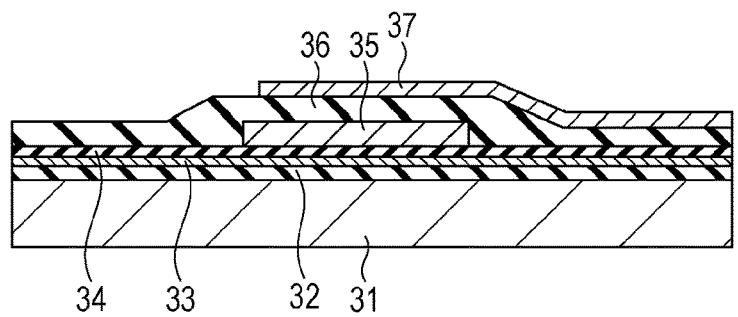

Subsequently, as illustrated in FIG. 9D, a second electrode 37 is formed. It is desirable that the second electrode 37 be formed of a material having a low residual stress. In addition, if a sacrifice layer removal step or a sealing step is performed after the second electrode 37 is formed, it is desirable that the second electrode 37 be formed of a material having a resistance to etching for the sacrifice layer and a heat resistance. To meet such a requirement, aluminum, an aluminum silicon alloy, or titanium, for example, can be employed.

Figure 9E:
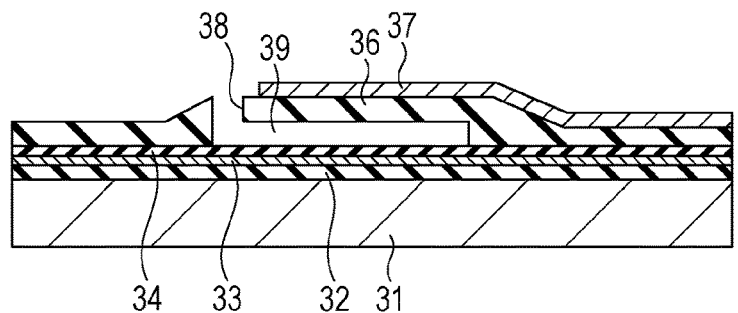

Subsequently, as illustrated in FIG. 9E, an etching hole 38 is formed in the second insulating film 36.

The etching hole 38 is used to introduce an etching solution or etching gas for removing the sacrifice layer 35 by etching.

Subsequently, the sacrifice layer 35 is removed to form a cavity 39. To remove the sacrifice layer 35, wet etching or dry etching can be employed. If chrome is used as the material of the sacrifice layer 35, wet etching is desirable.

If chrome is used as the material of the sacrifice layer 35, it is desirable that the second electrode 37 be formed of titanium to prevent the second electrode 37 from being etched during etching of the sacrifice layer 35.

If the second electrode 37 is formed of, for example, an aluminum silicon alloy, it is desirable that the insulating film be formed on the second electrode 37 using a material that is the same as the material of the second insulating film 36 after the second electrode 37 is formed and, thereafter, the etching hole 38 be formed to remove the sacrifice layer 35.

Figure 10A:
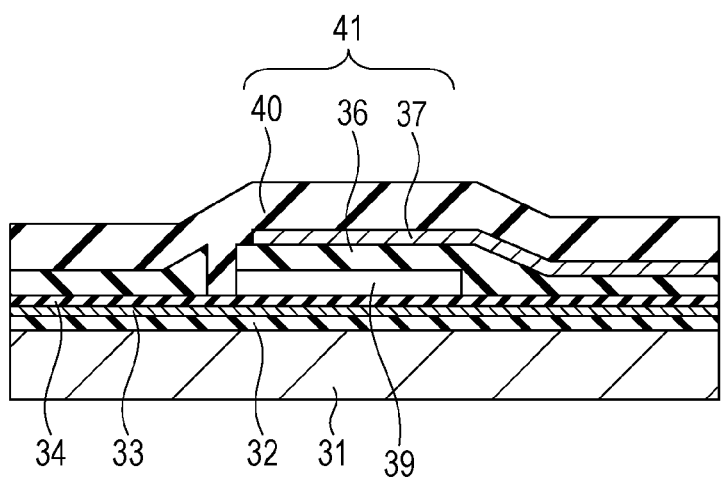
FIGS. 10A and 10B illustrate a method for manufacturing the capacitive micromachined ultrasonic transducer according to the present invention.

Subsequently, as illustrated in FIG. 10A, to seal the etching hole 38, a sealing film 40 is formed. A vibrating membrane 41 is formed from the second insulating film 36, the second electrode 37, and the sealing film 40. The sealing film 40 needs to prevent liquid or external air from entering the cavity 39.

If the internal pressure of the cavity 39 is the atmospheric pressure, the gas inside the cavity 39 inflates or deflates due to a variation of the temperature. In addition, since a high electric field is applied to the cavity 39, the reliability of the element may decrease due to ionization of molecules.

Accordingly, sealing needs to be performed under a reduced pressure. By reducing the pressure inside the cavity 39, the air resistance inside the cavity 39 can be reduced. In this manner, the vibrating membrane 41 can easily vibrate and, thus, the sensitivity of the capacitive micromachined ultrasonic transducer can be improved.

In addition, by performing the sealing, the capacitive micromachined ultrasonic transducer can be used in liquid. It is desirable that the sealing material be the same as the material of the second insulating film 36 to increase the adhesiveness. For example, the second insulating film 36 and the sealing film 40 can be formed of silicon nitride.

Figure 10B:
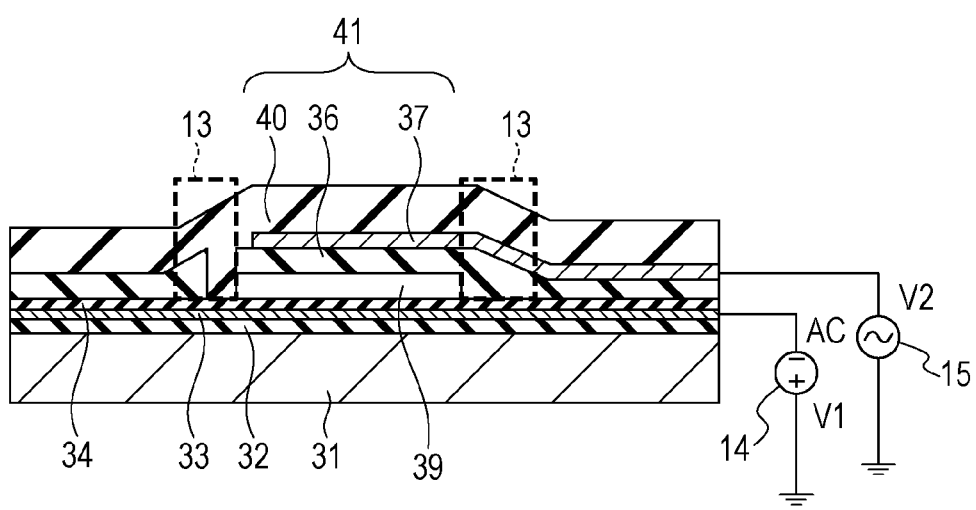

In FIGS. 10A and 10B, the configuration in which second electrode 37 is sandwiched by the second insulating film 36 and the sealing film 40 is illustrated as an example. However, after the second insulating film 36 is formed, the etching hole 38 may be formed. Thereafter, etching of the sacrifice layer 35 may be performed. Subsequently, the sealing film 40 may be formed and, thereafter, the second electrode may be formed.

If the second electrode 37 is exposed on the outermost surface, short circuit of the elements easily occurs due to a foreign substance, for example. Thus, it is desirable that the second electrode 37 be formed on the insulating film.

After the above-described steps are completed, the configuration illustrated in FIG. 10B is obtained. Thus, the capacitive micromachined ultrasonic transducer illustrated in FIGS. 1 and 2 can be produced.

The present invention is described in more detail below with reference to a particular exemplary embodiment and a comparative example.

First Exemplary Embodiment

The present exemplary embodiment is described below with reference to FIGS. 12 and 13.

Figure 12:
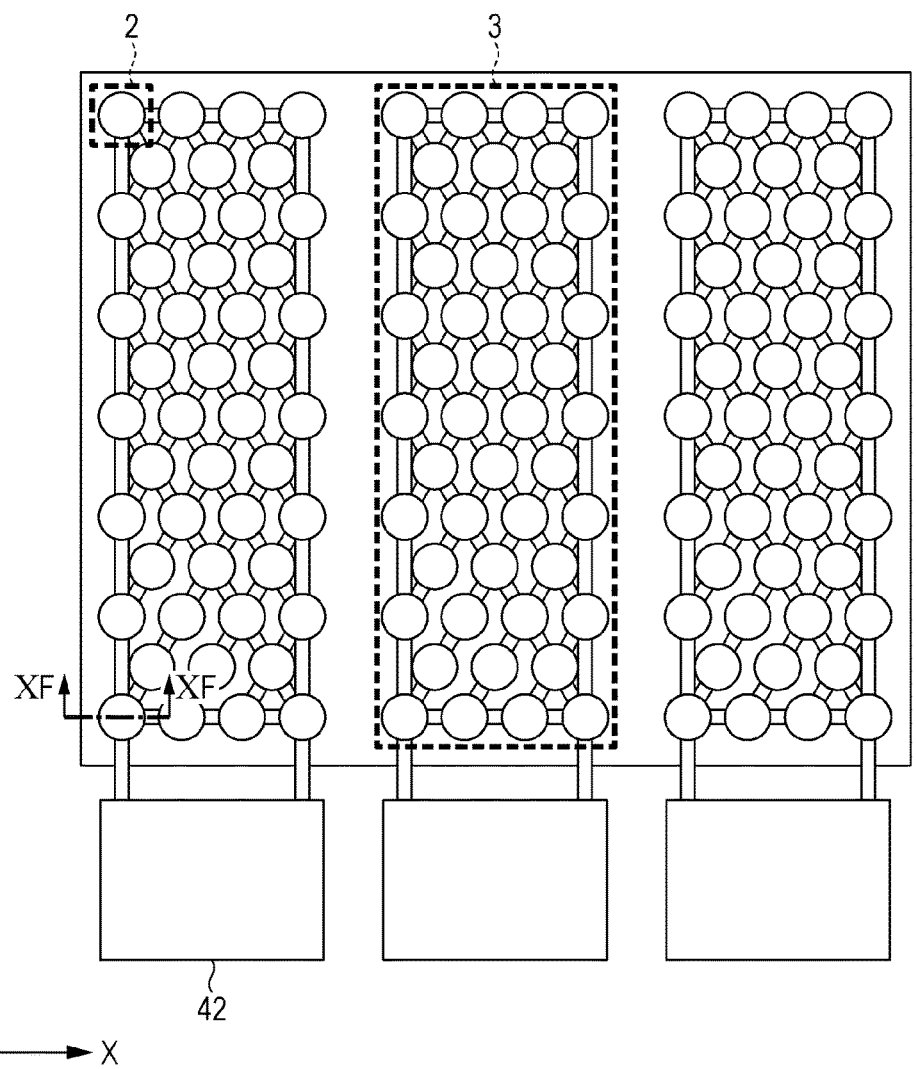
FIG. 12 is a top view of the capacitive micromachined ultrasonic transducer according to a first exemplary embodiment.
Figure 13:
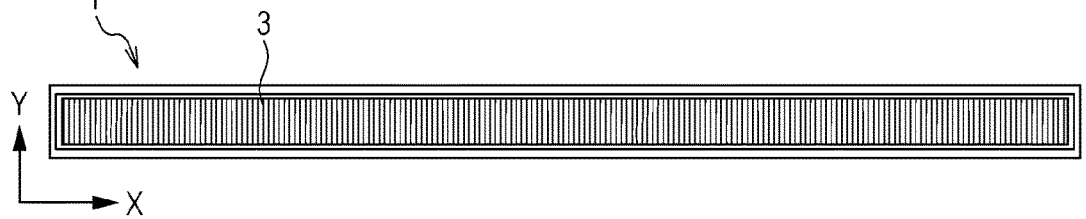
FIG. 13 is an enlarged view of FIG. 12 illustrating the capacitive micromachined ultrasonic transducer according to the first exemplary embodiment.

FIG. 12 is a top view of the capacitive micromachined ultrasonic transducer according to the present exemplary embodiment. FIG. 13 is a schematic enlarged view of FIG. 12.

The external dimension of the capacitive micromachined ultrasonic transducer 1 illustrated in FIG. 12 is 7.5 mm in the Y-direction and is 44 mm in the X-direction.

The external dimension of the element 3 is 0.2 mm in the X-direction and is 4 mm in the Y-direction. 196 elements 3 are arranged in a one-dimensional array. FIG. 13 is a schematic enlarged view of part of FIG. 12. A cross-sectional view taken along a line XF-XF of FIG. 12 corresponds to FIG. 10A.

Each of the cells 2 that constitute the element 3 is circular in shape. The diameter of the cavity (the cavity 39 in FIG. 10A) is 27 μm.

As illustrated in FIG. 12, the cells 2 are arranged so as to be disposed most densely. Every neighboring cells 2 that constitute one element 3 are arranged so as to have a 30-μm distance from each other. That is, the shortest distance between the cavities of the neighboring cells 2 is 3 μm.

Although the number of the cells 2 is not illustrated in FIG. 12, 702 cells 2 are disposed in one element 3, in reality.

Each of the cells 2 includes a silicon substrate having a thickness of 300 μm (the substrate 31 illustrated in FIG. 10A, and the same applies to the following description), the third insulating film 32 formed on the silicon substrate 31, the first electrode 33 formed on the third insulating film 32, and the first insulating film 34 formed on the first electrode 33.

In addition, the cell 2 includes the vibrating membrane 41 including the second electrode 37, the second insulating film 36, and the sealing film 40, the vibration membrane support member 13 that supports the vibrating membrane 41, and the cavity 39. The thickness of the cavity 39 is set to 250 nm.

The third insulating film 32 is formed from a silicon oxide film having a thickness of 1 μm. The silicon oxide film is generated by thermal oxidation.

The first insulating film 34 is formed from a silicon oxide film having a thickness of 225 nm. The silicon oxide film is generated by Plasma Enhanced Chemical Vapor Deposition (PE-CVD).

The first electrode 33 is formed of titanium having a thickness of 50 nm, and the second electrode 37 is formed of titanium having a thickness of 100 nm.

Each of the second insulating film 36 and the sealing film 40 is a silicon nitride film produced by the PE-CVD technique and has a tensile stress lower than or equal to 450 MPa. The second insulating film 36 is 400 nm in thickness. The sealing film 40 is 750 nm in thickness.

The produced capacitive micromachined ultrasonic transducer includes a voltage applying unit that applies the bias voltage to between the first electrode and the second electrode and a voltage applying unit that applies a transmission voltage to the second electrode.

The result of measurement of the voltage-current characteristics of the first insulating film 34 and the second insulating film 36 that constitute the element 3 is the same as that illustrated in FIG. 3.

The result of measurement of the first insulating film 34 and the second insulating film 36 indicates that the dielectric constant of the first insulating film is 4.45 and the dielectric constant of the second insulating film 36 is 6.8. The value obtained by dividing the relative permittivity of the second insulating film 9 by the relative permittivity of the first insulating film 7 is 1.528.

The ratio of a voltage applied to the first insulating film 34 to the voltage applied to between the first electrode and the second electrode is 0.462 (=V1/V) from Equation (8). The ratio of a voltage applied to the second insulating film 36 to the voltage applied to between the first electrode and the second electrode is 0.538 (=V2/V) from Equation (9).

In addition, the voltage that causes the dielectric breakdown of the first insulating film 34 is 249.35 V (=VV1) from Equation (10). The voltage that causes the dielectric breakdown of the second insulating film 36 is 297.4 V (=VV2) from Equation (11). Accordingly, the dielectric strength voltage of the element 3 is 249.35 V.

In addition, the result of measurement of the pull-in voltage of the element 3 and the resonance frequency in the atmosphere indicates that the pull-in voltage is 298 V and the resonance frequency is 23.1 MHz.

Since the dielectric strength voltage of the element 3 is 249 V and the pull-in voltage is 298 V, an element that allows a voltage that is 83.6% of the pull-in voltage to be applied thereto can be produced.

In addition, when a voltage of 200 V is applied to the element 3, the electric field strength applied to the first insulating film 34 is 4.11 (MV/cm), and the electric field strength applied to the second insulating film 36 is 2.69 (MV/cm).

At that time, the electric field strength of the first insulating film 34 is 80.3% of the electric field strength that causes the dielectric breakdown of the first insulating film 34 (6 (MV/cm)). In addition, the electric field strength of the second insulating film 36 is 67.3% of the electric field strength that causes the dielectric breakdown of the second insulating film 36 (4 (MV/cm)).

According to the example, since a relatively high voltage (83.6% of the pull-in voltage) can be applied, a transducer having a relatively high conversion efficiency from the received acoustic wave to an electrical signal and a relatively high conversion efficiency from an electrical signal to an acoustic wave can be provided.

According to the present invention, the amplitude of the vibrating membrane can be increased by applying a high voltage to between the first electrode and the second electrode while maintaining the dielectric strength voltage. In this manner, a large acoustic wave can be transmitted and received.

COMPARATIVE EXAMPLE 1

By changing the thickness of the first insulating film (the silicon oxide film) of the capacitive micromachined ultrasonic transducer of the first exemplary embodiment to 50 nm, a transducer is produced. The other configuration is the same as the configuration of the first exemplary embodiment.

The result of measurement of the voltage-current characteristic of the first insulating film and the second insulating film of the present comparative example is the same as that illustrated in FIG. 3.

The result of measurement of the dielectric constants of the first insulating film 34 and the second insulating film 36 indicates that the dielectric constant of the first insulating film is 4.45 and the dielectric constant of the second insulating film 36 is 6.8.

The ratio of a voltage applied to the first insulating film 34 to the voltage applied to between the first electrode and the second electrode is 0.160 (=V1/V) from Equation (8). The ratio of a voltage applied to the second insulating film 36 to the voltage applied to between the first electrode and the second electrode is 0.84 (=V2/V) from Equation (9).

In addition, the voltage that causes the dielectric breakdown of the first insulating film 34 is 160 V (=VV1) from Equation (10). The voltage that causes the dielectric breakdown of the second insulating film 36 is 190.5 V (=VV2) from Equation (11). Accordingly, the dielectric strength voltage of the element 3 is 160 V.

In addition, the result of measurement of the pull-in voltage of the element 3 and the resonance frequency in the atmosphere indicates that the pull-in voltage is 249 V and the resonance frequency is 23.1 MHz.

According to the present comparative example, the dielectric strength voltage of the element is 160 V while the pull-in voltage is 249 V. That is, only up to 64.25% of the pull-in voltage can be applied to the element.

Accordingly, the conversion efficiency (the conversion efficiency from the received acoustic wave to an electrical signal and the conversion efficiency from the electrical signal to an acoustic wave) is inferior to that of the first exemplary embodiment.

According to the capacitive micromachined ultrasonic transducer of the present invention, the electric field strength applied to the first insulating film is closer to the electric field strength that causes the dielectric breakdown than the electric field strength applied to the second insulating film.

In this manner, the capacitive micromachined ultrasonic transducer having an excellent dielectric strength voltage while maintaining the transmission sound pressure and sensitivity characteristic can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-242450 filed Nov. 28, 2014, which is hereby incorporated by reference herein in its entirety.

What is claimed is:

1. A capacitive micromachined ultrasonic transducer comprising:
    a first insulating film and a second insulating film disposed with a gap therebetween;
    a first electrode and a second electrode disposed on outer surfaces of the first and second insulating films, respectively, with the gap therebetween;
    at least one cell having an electrostatic capacitance between the first and second electrodes that varies with a variation of a thickness of the gap caused by displacement of the second insulating film and the second electrode; and a voltage applying unit configured to apply a voltage to between the first electrode and the second electrode, wherein an electric field strength applied to the first insulating film is closer to an electric field strength that causes dielectric breakdown of the first insulating film than an electric field strength applied to the second insulating film that causes dielectric breakdown of the second insulating film, wherein the first insulating film includes silicon oxide, and the second insulating film includes silicon nitride, and wherein a thickness of the second insulating film is greater than or equal to $0.32 \times G^{1.24}$, where G represents the thickness of the gap.

2. The capacitive micromachined ultrasonic transducer according to claim 1, further comprising:

an additional insulating film disposed on the second electrode, wherein the second insulating film, the second electrode, and the additional insulating film are displaceable.

3. The capacitive micromachined ultrasonic transducer according to claim 1, wherein the first insulating film is an insulating film having Fowler-Nordheim tunneling conduction characteristic.

4. The capacitive micromachined ultrasonic transducer according to claim 1, wherein the second insulating film is an insulating film having Poole-Frenkel conduction characteristic.

5. The capacitive micromachined ultrasonic transducer according to claim 1, wherein the first insulating film is formed of silicon oxide, and the second insulating film is formed of silicon nitride.

6. A test object information acquiring apparatus comprising:

an ultrasonic probe including the capacitive micromachined ultrasonic transducer according to claim 1;

an image processing unit;

a circuit unit configured to send and receive a signal between the ultrasonic probe and the image processing unit; and a control unit configured to control the image processing unit and the circuit unit.

7. The capacitive micromachined ultrasonic transducer according to claim 1, wherein the capacitive micromachined ultrasonic transducer comprises a plurality of cells each connected to the first electrode, and the cells constitute at least one element.

8. The capacitive micromachined ultrasonic transducer according to claim 7, wherein the capacitive micromachined ultrasonic transducer comprises a plurality of elements.

9. The capacitive micromachined ultrasonic transducer according to claim 1, wherein an electric field strength E1 applied to the first insulating film and an electric field strength E2 applied to the second insulating film are given as follows:

$$E1 = V/(t1 + t2 \times \in 1/\in 2), \text{ and}$$

$$E2 = V/(t2 + t1 \times \in 2/\in 1)$$

where V denotes a voltage applied to between the first electrode and the second electrode, t1 denotes the thickness of the first insulating film, t2 denotes the thickness of the second insulating film, $\in 1$ denotes the relative permittivity of the first insulating film, and $\in 2$ denotes the relative permittivity of the second insulating film, and wherein the following expression is satisfied:

$$E1/EX1 > E2/EX2$$

where EX1 denotes an electric field strength that causes dielectric breakdown of the first insulating film, and EX2 denotes an electric field strength that causes dielectric breakdown of the second insulating film.

10. The capacitive micromachined ultrasonic transducer according to claim 1, wherein a value obtained by dividing a relative permittivity of the second insulating film by a relative permittivity of the first insulating film is greater than 1.14.

* * * * *